(12) United States Patent
Sarfarazi

(10) Patent No.: US 6,423,094 B1
(45) Date of Patent: Jul. 23, 2002

(54) ACCOMMODATIVE LENS FORMED FROM SHEET MATERIAL

(76) Inventor: Faezeh M. Sarfarazi, 25 Wiswall Rd., Newton Center, MA (US) 02159

( * ) Notice: Subject to any disclaimer, the term of this patent is extended or adjusted under 35 U.S.C. 154(b) by 0 days.

(21) Appl. No.: 08/176,914

(22) Filed: Jan. 3, 1994

Related U.S. Application Data

(63) Continuation-in-part of application No. 07/793,470, filed on Nov. 18, 1991, now Pat. No. 5,275,623.

(51) Int. Cl.$^7$ .................................................. A61F 2/16
(52) U.S. Cl. ......................................................... 623/6.34
(58) Field of Search ........................ 623/6, 6.11, 6.32, 623/6.33, 6.34, 6.59

(56) References Cited

U.S. PATENT DOCUMENTS

| | | | | |
|---|---|---|---|---|
| 4,253,199 A | * | 3/1981 | Banko | 623/6 |
| 4,466,705 A | * | 8/1984 | Michelson | 623/6 |
| 4,685,922 A | * | 8/1987 | Peyman | 623/6 |
| 4,764,169 A | * | 8/1988 | Grendahl | 623/6 |
| 4,764,198 A | | 8/1988 | Grendahl | 623/6 |
| 4,790,847 A | * | 12/1988 | Woods | 623/6 |
| 4,842,601 A | * | 6/1989 | Smith | 623/6 |
| 4,883,485 A | * | 11/1989 | Patel | 623/6 |
| 4,902,293 A | * | 2/1990 | Feaster | 623/6 |
| 4,932,966 A | * | 6/1990 | Christie et al. | 623/6 |
| 4,946,469 A | * | 8/1990 | Sarfarazi | 623/6 |
| 4,950,289 A | | 8/1990 | Krasner | 623/6 |
| 5,123,905 A | | 6/1992 | Kelman | 606/107 |
| 5,275,623 A | * | 1/1994 | Sarfarazi | 623/6 |

FOREIGN PATENT DOCUMENTS

| | | | | |
|---|---|---|---|---|
| EP | 0162573 | * | 11/1985 | 623/6 |
| EP | 0328117 | * | 8/1989 | 623/6 |
| EP | 0337390 | * | 10/1989 | 623/6 |

* cited by examiner

*Primary Examiner*—David J. Isabella
(74) *Attorney, Agent, or Firm*—Bradford Kile, Esq.; Kile Goekjian Lerner & Reed PLLC

(57) ABSTRACT

Accommodative intraocular lens systems having two lenses or one lens and one ring connected by sections of the same material are manufactured from a sheet material, and then the connecting sections are bent to align the optical axis of the lenses. Accommodation is achieved either when the two lenses are moved closer and further from each other, or when the single lens is moved closer and farther from the retina of the eye.

17 Claims, 10 Drawing Sheets

ACCOMMODATIVE LENS FORMED FROM SHEET MATERIAL

This application is a Continuation-In-Part of U.S. patent application Ser. No. 07/793,470 filed Nov. 18, 1991 now U.S. Pat. No. 5,275,623.

FIELD OF THE INVENTION

This invention relates to intraocular lenses for implanting in the capsular bag of the posterior chamber of the eye after an anterior capsulorhexis. After implantation the lens makes use of the ciliary muscle to adjust the refractive power of the lens.

BACKGROUND OF THE INVENTION

Cataract extraction is the most common ophthalmic surgical procedure performed in the United States. Extracapsular cataract extraction involves cutting a portion of the anterior capsule (anterior capsulorhexis) followed by removal of the nucleus. Alternatively, a probe may be inserted through the anterior capsule and ultrasonically vibrated, transforming lens material into an emulsion is then irrigated and aspirated from the capsular bag (phacoemulsification). After removal of the natural lens, images no longer focus on the retina and a replacement lens must be provided for clear vision. Replacement lenses can be glasses, contact lenses or intraocular lenses. Of these, intraocular lenses give the greatest convenience and undistorted vision, however, for insertion of a lens, the size of the incision is dictated by the size of the implant rather than requirements of removing the natural lens. Replacement lenses, however, lack the ability of a natural lens to accommodatively focus on near and far objects.

When a person looks at an object, light is reflected from the object through the cornea, the aqueous humor, through the pupil and into the lens which converges the light through the vitreous body onto the retina. To clearly focus on near objects, light rays must be bent more. To accomplish this the lens becomes more curved and thicker. Most of this change comes from pulling and relaxing the capsular bag at its equator. The equator of the bag is attached to the ciliary muscle by filaments called the zonules of Zinn which are in turn attached to the ciliary muscle. When looking at an object in the distance, the ciliary muscle relaxes and expands, thereby pulling on the zonules, flattening the capsule and lens. When looking at a near object, the ciliary muscle tenses and contracts moving the muscle sightly inward and relaxing the pull on the zonules, allowing the capsular bag to become more curved and thickened from front to back. The lens itself is composed of interlocking fibers which affect the elastic movement of the lens so that as the lens changes shape the fibers alter their curvature. As a person ages, the accommodative ability of the lens decreases which changes in the eye. Age related eye changes include thickening of the lens, an increase in the amount of insoluble protein in the lens, a migration in the points of attachment of the zonules away from the equator of the capsule, and partial liquefaction of the vitreous body.

Lenses are made from transparent material having the shape of a body of rotational symmetry, such as a sphere. The degree of curvature of the surface is inversely proportional to the radius of curvature and the focal length. Parallel light rays converge after being refracted through a convex surface and diverge after being refracted through a concave surface. Refractive power of a lens is dependent upon the refractive index of the lens material and the lens curvature.

A simple lens has two sides, each with a curvature. Two lenses separated by a given distance, can be considered as one thick lens having two foci and two principal planes. The focal length of the system is the product of their focal lengths ($f_1, f_2$) divided by the sum of their focal lengths minus the distance (d) between them i.e.

$$F=(f_1 f_2)/(f_1+f_2-d)$$

When the space between the lenses is not a vacuum but contains a substance, the amount substracted from the sum of the focal length is divided by the refractive index (n) of that substance.

$$F=(f_1 f_2)/(f_1+f_2-d/n)$$

The refractive power of a lens system is given by the inverse of the focal length. By using two fixed lenses and varying the distance between them, a system of variable focal length can be constructed. If the curvature of one or both of the lens surfaces increases as the distance between lenses is increased, and decreases as the distance between the lenses is decreased, the change in focal length is enhanced.

Several attempts have been made to provide the eye with focal length accommodation. The most familiar of these is a bi or multi-focal lens. These are used in glasses, contacts, and intraocular lenses but have a disadvantage in that the focal accommodation is dependent upon direction of focus.

U.S. Pat. No. 4,254,509 discloses a lens which takes advantage of the ciliary muscle. However, this lens is placed in the anterior chamber of the eye. Such implants are at times accompanied by complications such as damage to the vascular iris.

U.S. Pat. No. 4,253,199 discloses a lens attached directly to the ciliary body. The lens is in a more natural position but requires suturing to the ciliary body risking massive rupture during surgery and bleeding from the sutures.

U.S. Pat. No. 4,685,922, incorporated herein by reference, discloses a chambered lens system for which the refractive power can be changed. Such alteration is permanent, accomplished by rupture of the chambers.

U.S. Pat. No. 4,790,847 provides a single lens for in capsular bag implantation using rearwardly biased haptics which engage the capsular bag at its equator and move the lens forward and backward upon contraction and relaxation of the ciliary muscles.

U.S. Pat. No. 4,842,601, incorporated herein by reference, discloses a two section deformable lens assembly for implanting in the capsular bag. The lens allows division of refractive power and takes advantage of the action of the ciliary body and zonules on the capsular bag. This lens system is assembled after insertion.

U.S. Pat. No. 4,892,543 discloses another two lens assembly for placement in the posterior chamber, possibly in the bag where the capsular bag is not removed. This lens allows dividing the refractive power between two lenses and introduces a variable focal length in one of the lenses by compressing a flexible wall of one lens against the convex surface of the second fixed lens. This requires that the first and second lens be in substantially adjacent positions.

U.S. Pat. No. 4,932,966, incorporated herein by reference, presents an accommodative lens in which two lenses joined at their periphery enclosed a fluid filled sack, accommodation being accomplished selectively changing the fluid pressure in the sac. One lens is a rigid base lens and the other lens is membrane-like, the equatorial diameter of the lens assembly being substantially that of a dilated pupil and is supported by bladders or haptics.

BRIEF SUMMARY OF THE INVENTION

The present invention provides dual and thick lens optics, capable of accommodating focus at a range of distances in a simple unitary structure. It uses the eye capsule's natural shaping from the ciliary body to accommodate the focus. Embodiments provide for insertion into a small incision, natural centricity, and increased focusing of the components.

DESCRIPTION OF THE PREFERRED EMBODIMENTS

Figure 1:
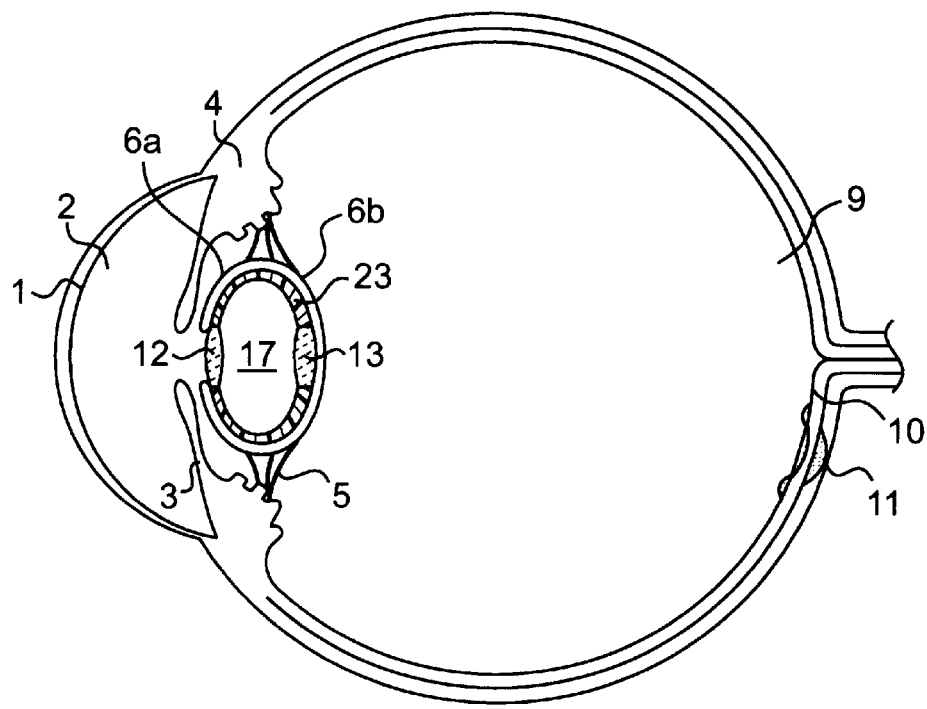
FIG. 1 is a cross sectional view of the eye with an accomodative lens of the invention in place.
Figure 2:
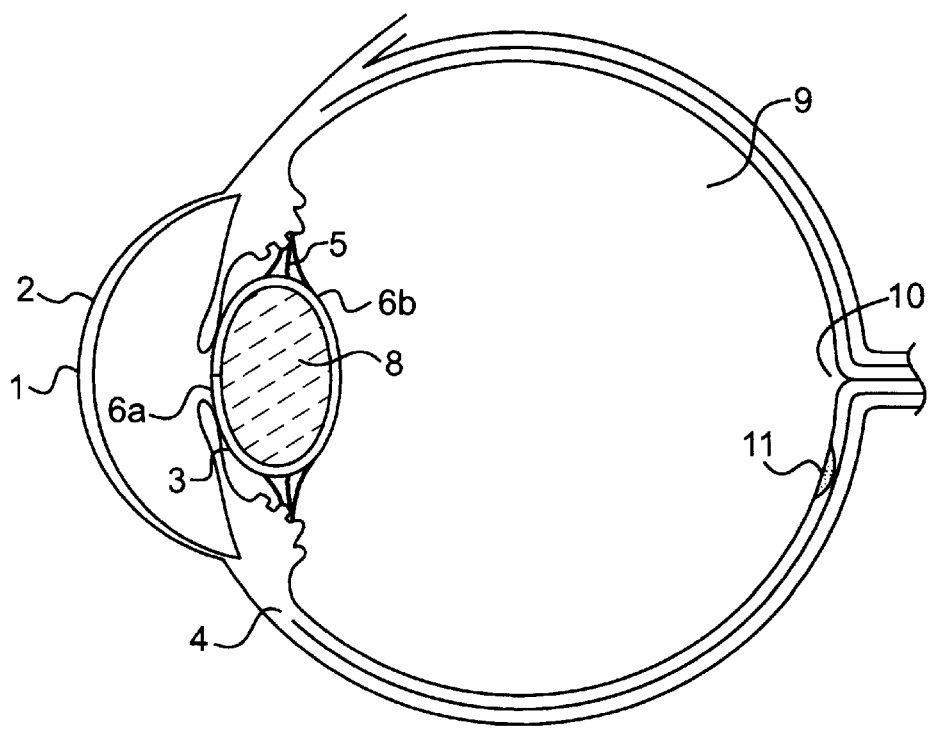
FIG. 2 is a vertical sectional view of an eye.

FIG. 2 shows a cross section of the eye. As light enters the eye it passes through the cornea 1; through the aqueous humor in the anterior chamber 2; through the pupil located centric of iris 3; through the anterior wall of the capsular bag 6a; is convergently refracted by the lens 8; passes through the posterior wall of capsular bag 6b; through the vitreous humor 9 to the retina 10 at the fovea 11. The shape of the lens capsule is controlled by ciliary muscle 4 attached to the capsule by filaments called zonules 5.

Figure 6:
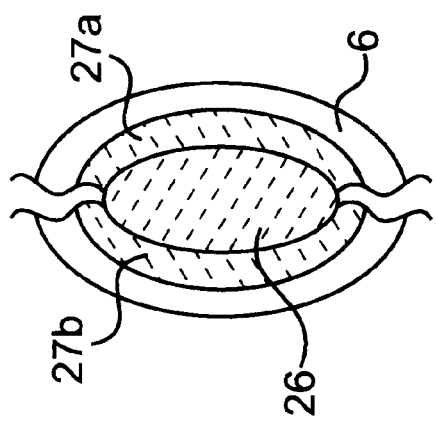
FIG. 6 is a schematic side view of the natural lens

The natural lens, shown in FIG. 6, has a central biconvex nuclear portion 26 surrounded by a concavo-convex menisci 27 a and b. Lenses which are bi convex converge light rays. Lenses which are concavo-convex have a diverging effect on light rays. Therefore the menisci of the natural lens provides a moderating effect on the converging nucleus. The anterior-posterior or polar diameter of the lens is about 5 mm. The equatorial diameter is about 9 mm.

Figure 4:
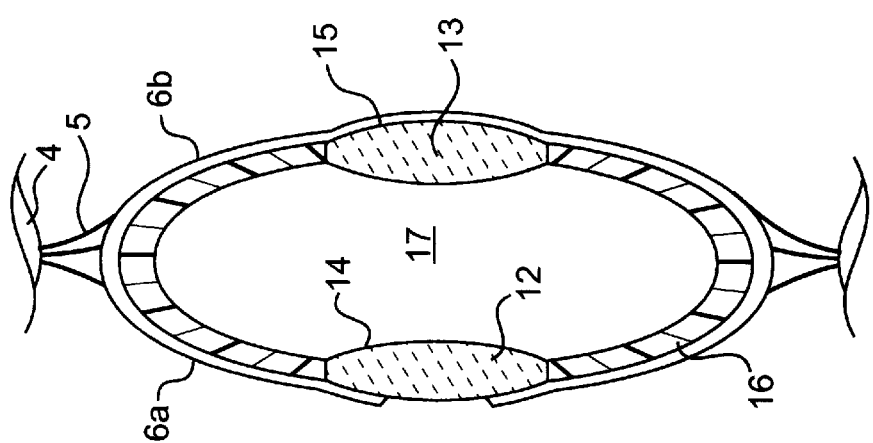
FIG. 4 is a partial sectional view showing the intraocular lens of FIG. 3 when the eye is focused on a distant object.
Figure 3:
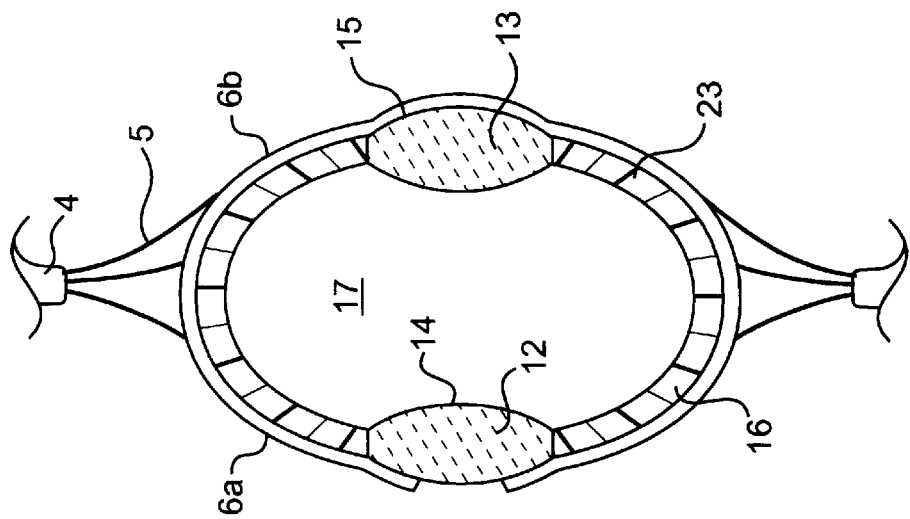
FIG. 3 is a partial sectional view showing an intraocular lens in accordance with the invention within the capsular bag when the eye is focused on a near object.

When the natural lens 8 is removed through capsulorhexis 25, the intraocular implant shown in FIGS. 3 and 4 can restore focusing. The implant has an anterior lens 12 with an anterior surface 14 and a posterior lens 13 with an posterior surface 15. Extending from and connecting the equatorial perimeters of the anterior and posterior lenses i a flexible cell wall 16 forming a discoid cell 17 having an equatorial diameter substantially the same as the capsule 6. Cell 17 formed by the two lenses 12 and 13 is filled with a fluid (gas or liquid) such as air after implantation. Pressure around the equator of the cell supports the lens assembly in place.

Figure 8:
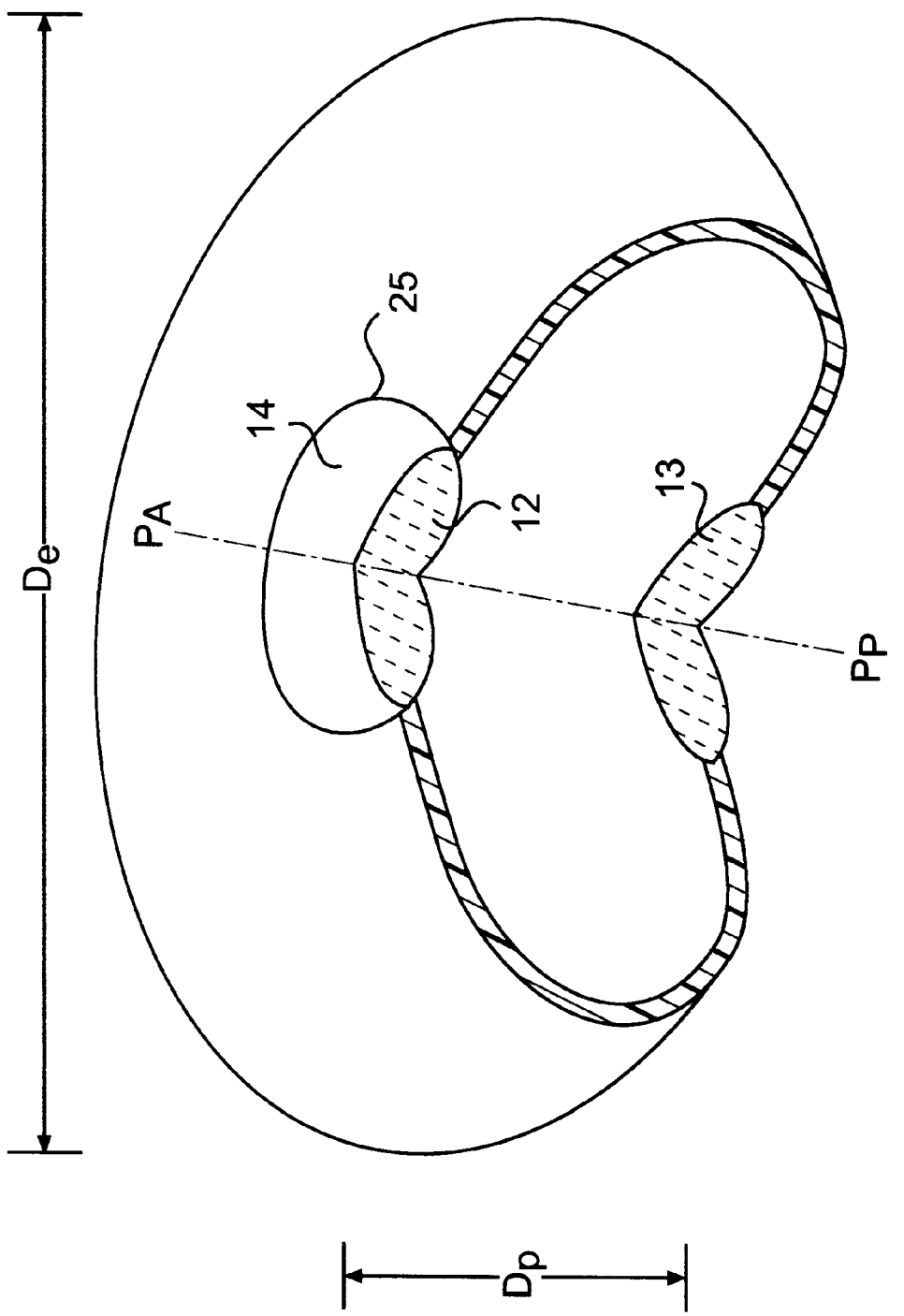
FIG. 8 is a perspective sectional view of the embodiment of FIG. 3.

FIG. 8 shows the same lens assembly having a cell equatorial diameter of $D_e$, a cell polar diameter of $D_p$, and a polar axis $P_aP_p$. The equatorial perimeter 24 of the anterior lens 12 is substantially the size of a pupil (4–5 mm.).

Although the lenses may be rigid or flexible, flexible lenses can provide greater accommodation. Anterior and posterior lenses, if rigid can be made out of a biocompatible, transparent material such as PMMA (polymethyl methacrylate), HEMA (hydroxyethyl methacrylate), polysulfones, polycarbonates, or a silicon polymer (polydimethyl siloxanes). Materials for a soft lens would include gel forming polymers such as silica hydrogels, polysaccharides such as hyaluronic acid, or a transparent, lens-shaped sack of polyvinyl alcohol. The equatorial diameter of the anterior lens is about the size of a dilated pupil or 5 mm. Posterior and anterior lenses have a thickness of 1 to 1.5 mm. For a typical eye the anterior radius of curvature for the anterior lens is between 8 and 14 mm., and the posterior radius of curvature for the posterior lens is between 4 and 7 mm. The curvature of both faces of each lens can be altered to correct for differences in the shape of the eye (i.e. myopia). Since both lenses are converging lenses with a space between them, focal length and power is divided between them, however, if desired, the power could be in one lens. The cell wall 16 has a thickness of 0.1 mm., and can be made of a methacrylate, silicon polymer or other biocompatible, flexible material. The discoid shape is preferably an ellipsoid having a polar diameter of about 5 mm, and an equatorial diameter of 9 mm. when filled. When the ciliary muscles 4 relax and swell, the zonnules 5 pull on the equator of the capsule 6, the lens assembly flattens increasing its equatorial diameter and decreasing its polar diameter thus decreasing the distance between the two lenses and altering the power of the lens assembly. If the lenses are made from a soft material, such as a lens shaped sack filled with polyvinyl alcohol, they also pull into a flatted form enhancing optical power change. To facilitate inserting the lens assembly through an incision, soft lenses could be made of a gel forming polymer and dehydrated (thus shrinking them) and the cell left unfilled until after insertion. After insertion fluids from the surrounding tissue could reconstitute the lenses and fill the cell. The cell could also be filled with a microtube or hypodermic.

Figure 5:
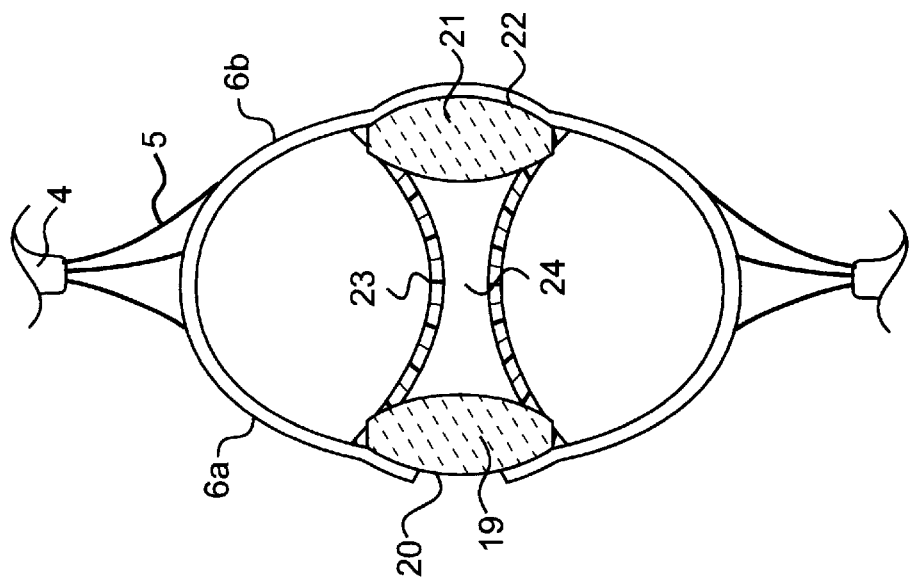
FIG. 5 is a partial sectional view showing an alternate embodiment.

FIG. 5 shows an alternative form of the invention. In capsular bag 6 is a lens assembly having an anterior lens 19 with anterior curved surface 20 and a posterior lens 21 with posterior curved surface 22. Extending from and connecting the equatorial perimeters of the anterior and posterior lenses is a flexible, resilient cell wall 23 having a diameter substantially the same as lenses 19 and 21. The substantially paraboloid cell 24 thus formed may be filled with a fluid (gas or liquid) such as air. Two or more resilient haptics may be substituted for the cell wall to space the lenses and bias them against the capsular poles. The springlike action of the haptics or cell wall bias the lenses against the surface of the capsular poles supporting the lens assembly in place. As the capsular bag is pulled and released by the ciliary muscles, the lenses approach and withdraw from each other to provide focal accommodation. If a soft lens is used a support ring may be provided around the equator of the lens.

Figure 7:
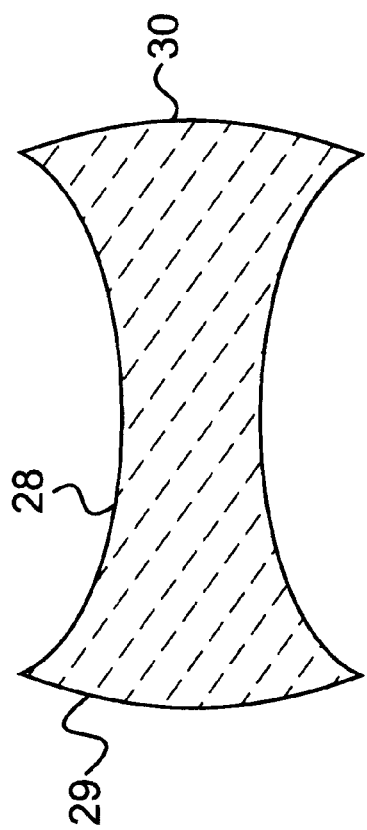
FIG. 7 is a side view of a thick lens embodiment of the lens assembly.

FIG. 7 shows an embodiment of the invention comprising a thick lens having an anterior surface 29 and a posterior surface 30. The body of the lens 28 is substantially paraboloid. Paraboloid for the purposes of this invention includes cylindrical, hyperboloid and paraboloid. The lens is made of a resilient material to bias the anterior and posterior surfaces against the capsular poles. This springlike action supports the lens in place such that when the capsular bag is pulled and released, the anterior and posterior surfaces approach and withdraw from each other providing focal accommodation.

The lens assemblies shown in FIGS. 5 and 7 can be inserted through an incision substantially the width of the lens then turned or be compressed for insertion.

Figure 9A:
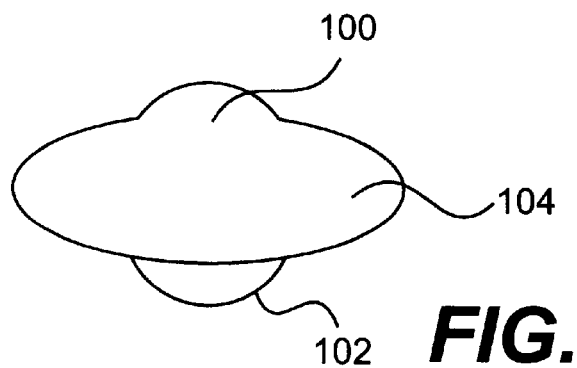
FIGS. 9A and 9B are side and top views of an alternate unitary lens assembly.
Figure 11:
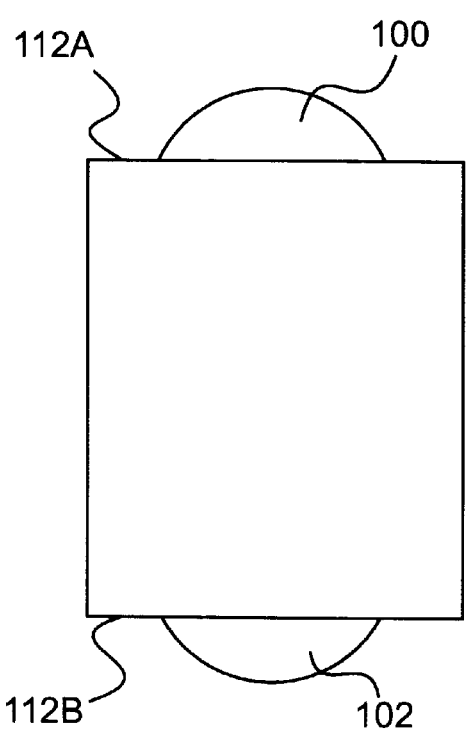
FIG. 11 is a side view of shouldered cylindrical unitary lens.
Figure 10:
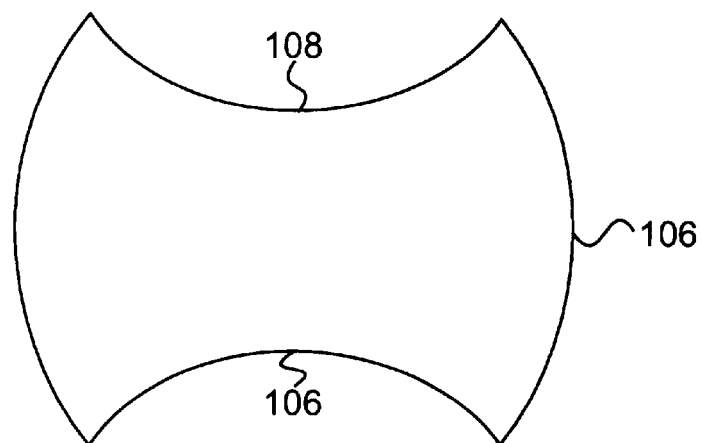
FIG. 10 is side view of concave unitary lens.
Figure 12:
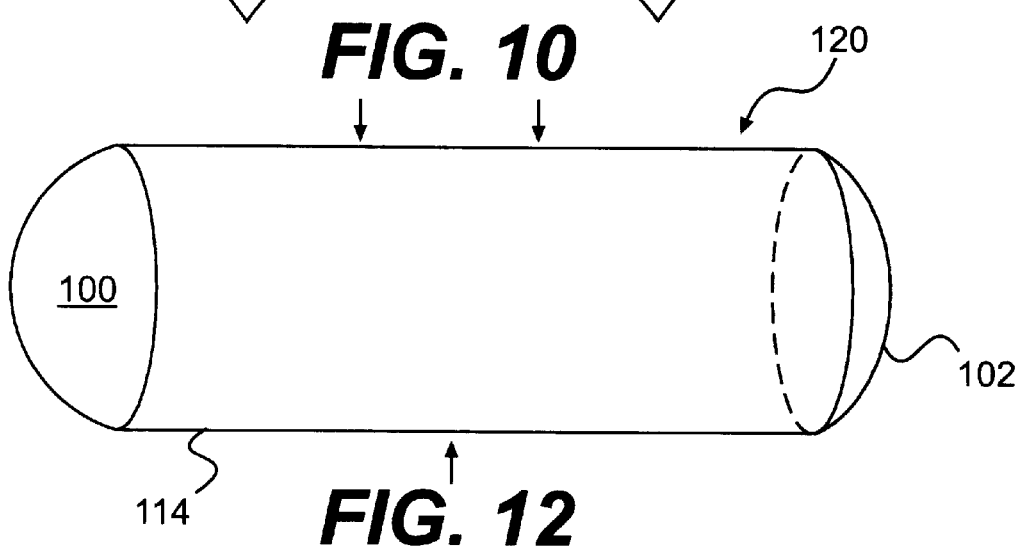
FIG. 12 is a side view of a cylindrical unitary lens.
Figure 13A:
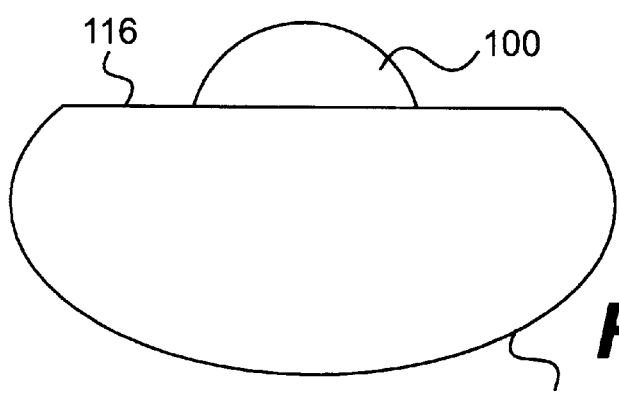
FIGS. 13A and 13B are side and top views of a single shouldered unitary lens.
Figure 13B:
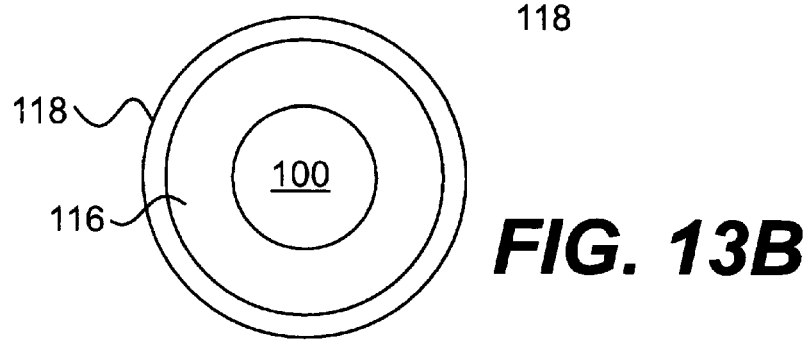

The unitary lens assembly of FIGS. 9A and B has anterior 100 and posterior 102 lens surfaces and a bulged bag engaging central section 104. The lens assembly is molded in one piece from a compressible optically transparent material such as a hydrogel, silicon rubber and soft acrylics. The lens of FIG. 10 has a rounded central section 106 between the anterior 108 and posterior 110 concave lens surfaces. The lens of FIG. 11 has annular ridges 112A and 112B to engage the capsular bag 6A, 6B. FIG. 12 shows a lens having a cylindrical body 114, and is preferably used where the lens is inserted through a lateral capsular incision. The lens of FIGS. 13A and 13B has a single shoulder 116 and a body which forms a continuous curved surface 118 which includes a posterior lens surface.

Figure 14:
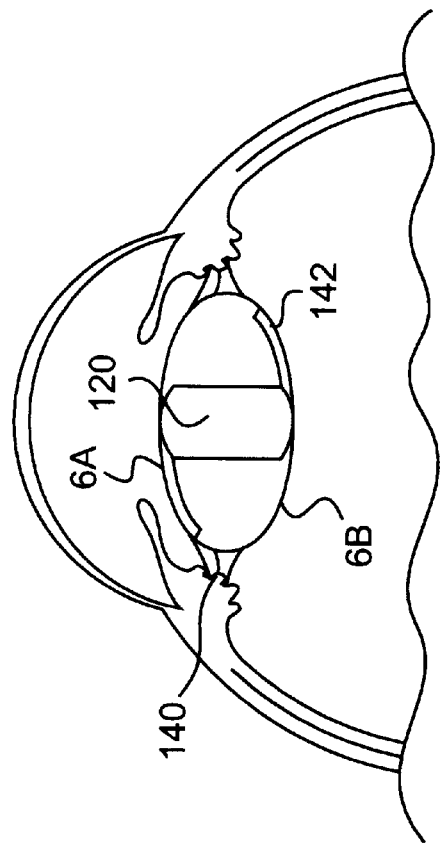
FIG. 14 is a side view of a lens being inserted into a capsular bag in which the lens has been removed through a side opening.
Figure 15:
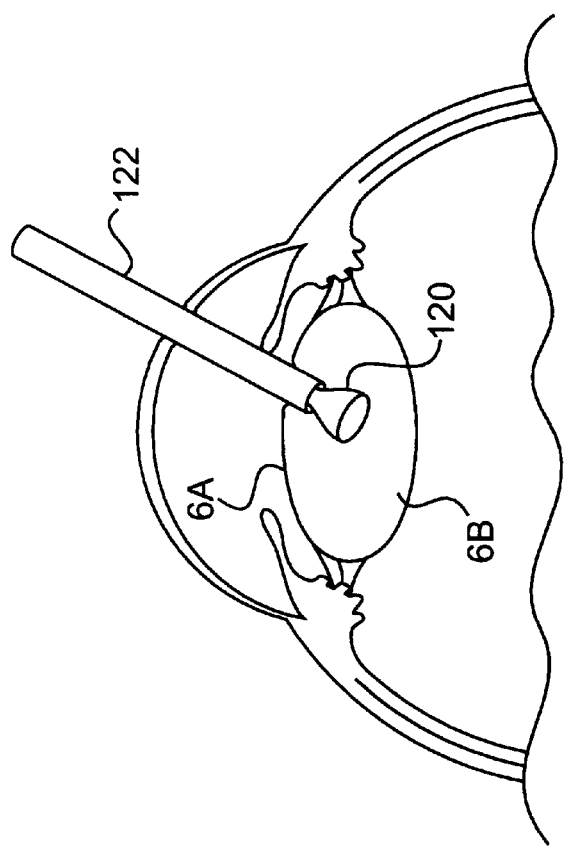
FIG. 15 is a side view of a cylindrical lens located in the capsular bag.

FIG. 14 shows a detail of the lens of FIG. 12 as placed inside the capsular bag. To insert the lens, the lens 120 is compressed laterally and placed in a tube 122 similar to U.S. Pat. No. 5,123,905, incorporated herein by reference, or by specialized forceps such as shown in U.S. Pat. No. 4,950, 289, incorporated herein by reference. The tube 122 is placed into the bag 6A, 6B and the lens 120 is forced out of the needle gently into the bag. For adequate compression, it is desirable to have a high degree of compressibility and memory in the material, or be able to dehydrate the material. Common hydrogels offer this possibility, but may lack a sufficient index of refraction necessary for proper magnification, however, means for altering the index of refraction exist such as incorporation of a solute into the hydrogel, and such hydrogels are becoming available. Alternatively a very compressible clear silicone compound may be suitable. To increase the index of refraction and to further reduce deformation of the lens surface, the surface may be provided with a thin coating of a harder material such as quartz or PMMA, as is now done in glasses. The lens shown in FIG. 15 has a cylindrical body 120 and a set of C shaped haptics 140, 142 to provide greater positional stability.

Figure 9B:
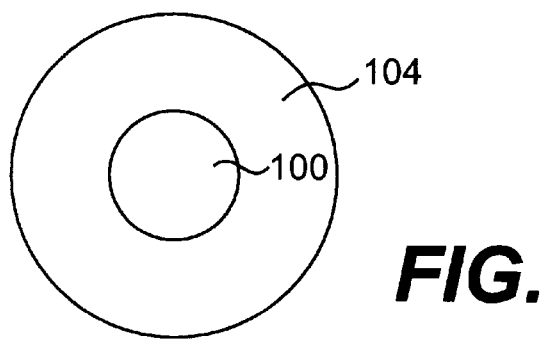
Figure 16:
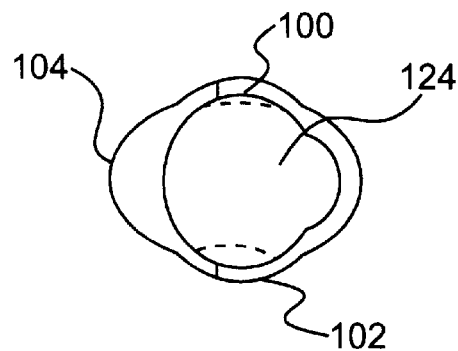
FIG. 16 is a cutaway view of of a hollow unitary lens.

The lens of FIG. 16 is similar to that of FIG. 9 except the center 124 is hollow. This allows greater compressibility for insertion.

Figure 17A:
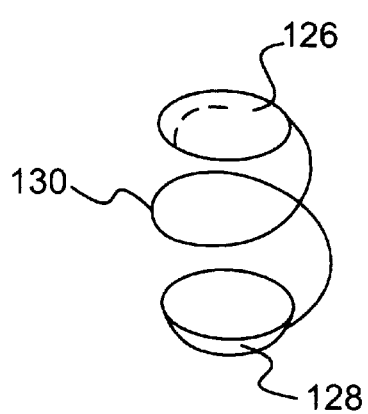
FIGS. 17A and 17B are perspective views of accommodative lenses with FIG. 17A is shown without haptics and FIG. 17B is shown with haptics a helical lens connection.
Figure 17B:
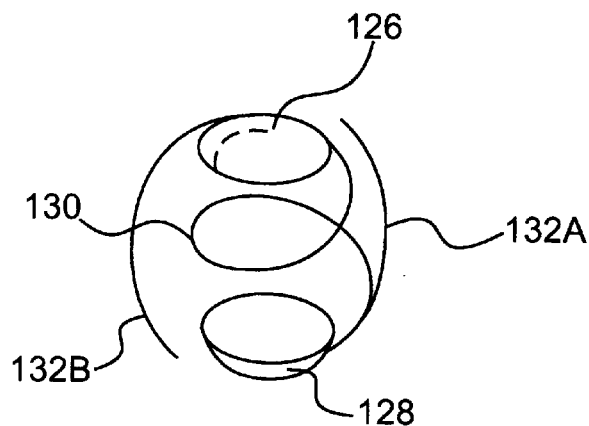

The lens of FIGS. 17A and 17B has anterior 126 and posterior 128 lenses connected by a compressible helix 130. The lens of 17B is provided with bag engaging haptics 132A and 132B.

Figure 18A:
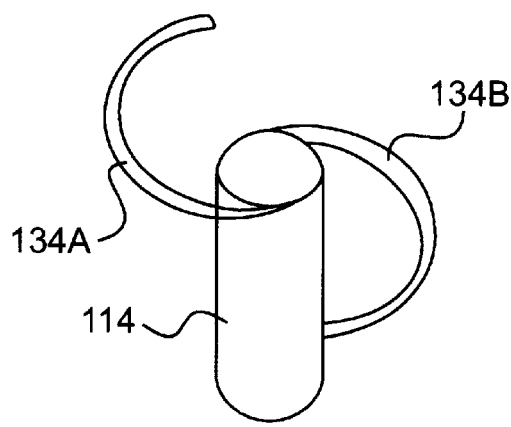
FIGS. 18A and 18B are perspective and side views of cylindrical lenses having haptics.
Figure 18B:
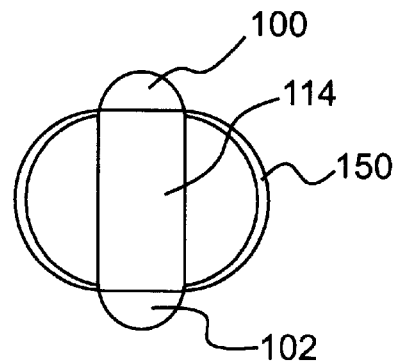

The lens of FIG. 18A is similar to that of FIG. 12, however, it is provided with haptics 134A, 134B to stabilize the lens. FIG. 18 B shows an alternative haptic 150 which extends from and connects the anterior 100 and posterior 102 lenses.

Haptics may be attached to either anterior or posterior surfaces, but should be very flexible to allow for compression into a tube.

Macular degeneration requires a very strong lens. Single lenses offer an optical change of about 30 diopters, two lenses can provide up to 60 diopters. However, the greater the magnification, the smaller the field of vision. Presently this is treated by a lens placed in front of the eye (glasses). However, by moving the posterior surface of the magnifier towards the retina, the field of vision can be increased and thus a lens assembly having two lens surfaces such as proposed here could be used for treatment of macular degeneration. Similarly, treatment of severe myopia (nearsightedness) could be treated by use of a convex surface on the posterior and/or anterior lens surfaces.

Figure 19A:
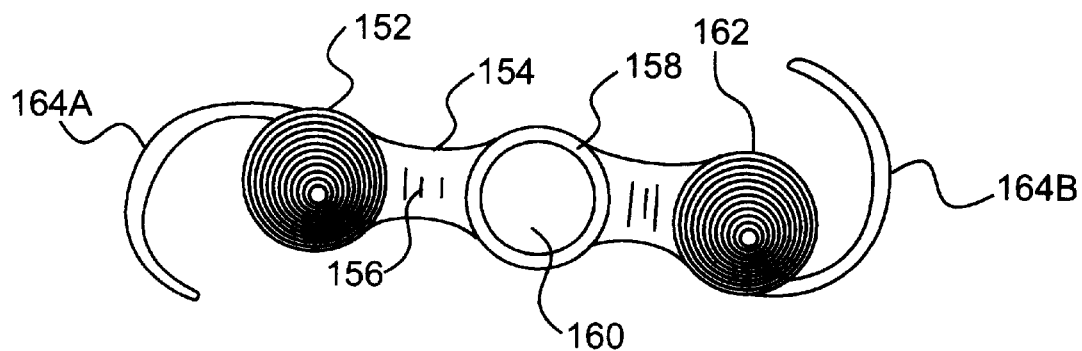
FIGS. 19A, 19B, are top views of an accommodative lens manufactured from sheet material before bending.
Figure 19B:
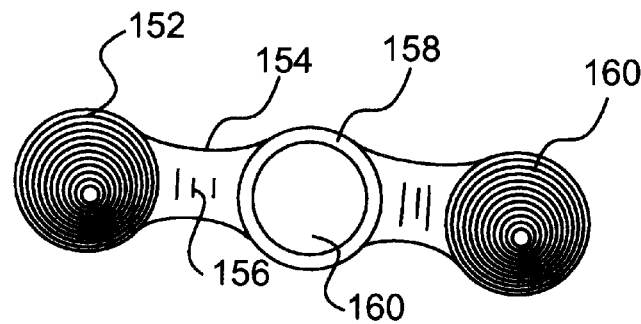
Figure 19C:
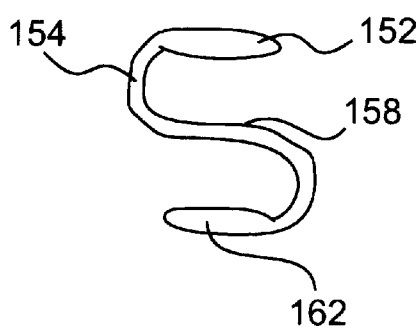
FIGS. 19C and 19D are side views of accommodative lenses manufacture from sheet material after bending.

FIGS. 19A, B, C, D show a lens which can be made from a sheet material with some resiliency such as thin acrylic. The anterior 152 and posterior 162 lenses are Fresnal type lenses. These lenses can be provided with haptics 164A, 164B. A central ring 158 has an opening 160 to allow vision between the anterior and posterior lenses 152, 162. A bridge 154 connects the lenses with the central section. The bridge 154 is provided with creases 156 for easier bending into as form shown in FIG. 19C. FIG. 19B shows a similar lens having no haptics.

Figure 19D:
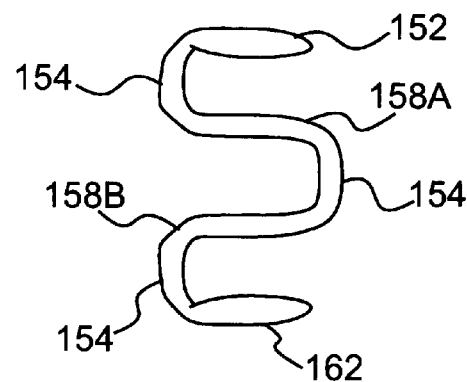

To provide more spring, the lens of FIG. 19D has been provided with a second central ring 158. Several such sections are possible. The lens would also work if only the anterior lens were a fresnal lens since it would move towards and away from the retina.

Figure 20A:
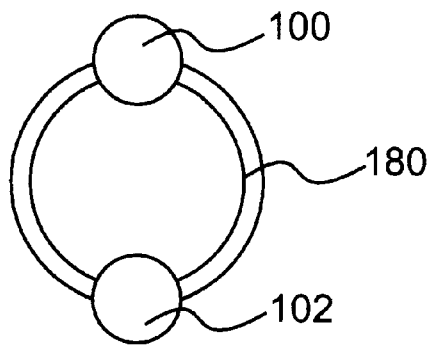
FIGS. 20A, 20B, and 20C are a top and two side views of a lens manufactured from sheet material.
Figure 20B:
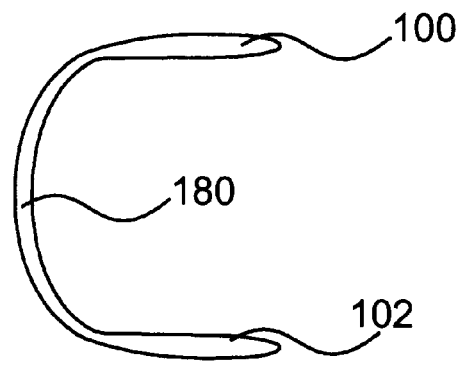
Figure 20C:
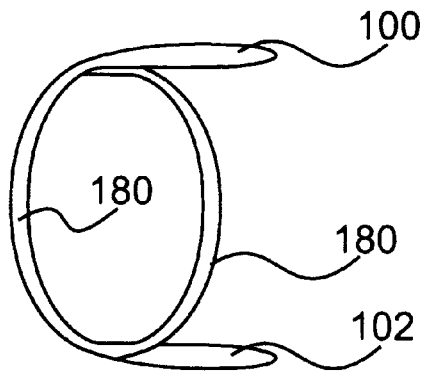

FIGS. 20A, B, and C show an alternative lens made from sheet material. The lenses 100, 102 are connected by a ring 180. When bent so that the anterior 100 and posterior lenses are located so that the optical axes are aligned, the ring 180 serves to engage the bag. Both halves of the ring may bend in the same direction as shown in FIG. 20 B or opposite directions as shown in FIG. 20C.

The principle of this lens could be adapted into a toy for children to learn about lenses and accommodation by making a pillow with the same features of this lens. The material for this pillow is a special transparent compressible material. Handles located on the greatest circumference could be incorporated into the design. Pulling the handles outward decreases the magnification Releasing or pushing the handles inward would increase the magnification so that it becomes an educational toy.

What is claimed is:

1. A single piece, accommodative intraocular lens system comprising:
   a first transparent structure, wherein said first transparent structure is an optic lens, said lens having a first surface, a perimeter and a second surface, said lens having a central optical axis;
   a second transparent structure, wherein said second transparent structure is an optic lens, said optic lens having a first surface, a perimeter and a second surface, said optic lens having a central optical axis;

a deformable connector extending between said perimeter of said first transparent structure, and said perimeter of said second transparent structure, said connector being formed by a circular ring and being integral at one peripheral location of said circular ring with said first transparent structure and being integral at a diametrically opposite peripheral location of said circular ring with said second transparent structure; and said optic lenses being formed from a single sheet of material with the optic axis of said lens bodies being substantially parallel in a generally flat manufactured posture and being operable when said deformable connector is bent to be coaxial when placed within a capsular bag of a human eye to provide an accommodative one piece intraocular lens system.

2. A single piece, accommodative intraocular lens system as defined in claim 1 wherein:

said circular band integrally joining a peripheral edge of said first and second optic lenses on opposite peripheral edges of said first and second optic lenses.

3. A single piece, accommodative intraocular lens system as defined in claim 1 and further comprising:

a second circular ring comprising a deformable connector extending between a perimeter location of said first transparent structure and a perimeter location of said second transparent structure.

4. A single piece, accommodative intraocular lens system as defined in claim 1 wherein:

said lens system is formed from a single sheet of PMMA material.

5. A single piece, accommodative intraocular lens system as defined in claim 1 wherein:

said lens system is formed from a polymer chosen from the group consisting of methacrylates, polycarbonates, siloxanes and polysulfones.

6. A single piece, accommodative intraocular lens system as defined in claim 1 wherein:

said lens system is formed from a material chosen from the group consisting of gel forming polymers and polyvinyl alcohols.

7. A single piece, accommodative intraocular lens system as defined in claim 1 wherein:

said lens system is formed from a material chosen from the group consisting of hydrogel, silicon rubber and soft acrylics.

8. A single piece, accommodative intraocular lens system as defined in claim 1 wherein:

said lens system is formed from a material comprising a silicone compound.

9. A single piece, accommodative intraocular lens system as defined in claim 1 wherein:

said optic lenses are provided with a surface coating selected from the group consisting of quartz and PMMA.

10. A single piece, accommodative intraocular lens system comprising:

a first transparent structure, wherein said first transparent structure is an optic lens, said lens having a first surface, a perimeter and a second surface, said lens having a central optical axis;

a second transparent structure, wherein said second transparent structure is an optic lens, said lens having a first surface, a perimeter and a second surface, said optic lens having a central optical axis;

a deformable connector extending between said perimeter of said first transparent structure, and said perimeter of said second transparent structure, said deformable connector including at least one circular ring and said deformable connector being integral with said perimeter of said first transparent structure and being integral with said perimeter of said second transparent structure; and said optic lenses of said first transparent structure and said second transparent structure being formed from a single sheet of material with the optic axes of said lens bodies being substantially parallel in a generally flat manufactured posture and being operable when said deformable connector is bent to be generally coaxial when placed within a capsular bag of a human eye to provide an accommodative one piece intraocular lens system.

11. A single piece, accommodative intraocular lens system as defined in claim 10 wherein:

said lens system is formed from a material comprising a silicone compound.

12. A single piece, accommodative intraocular lens system as defined in claim 10 wherein:

said lens system is formed from a material comprising PMMA.

13. A single piece, accommodative intraocular lens system as defined in claim 10 wherein:

said lens system is formed from an acrylic material.

14. A single piece, accommodative intraocular lens system as defined in claim 10 wherein:

said optic lenses of said first transparent structure and said second transparent structure are composed of Fresnal surface lenses.

15. A single piece, accommodative intraocular lens system as defined in claim 10 wherein:

said deformable connector comprises a central circular band and a first bridge member extending between a perimeter of said circular band and the perimeter of said first transparent structure and a second bridge member extending between an opposing location of the perimeter of said circular band and the perimeter of said second transparent structure.

16. A single piece, accommodative intraocular lens system as defined in claim 15 and further comprising:

an actuate haptic extending outwardly from the perimeter of each of the lens optics of said first transparent structure and said second structure for providing supporting engagement with an interior surface of a capsular bag of a human eye.

17. A single piece, accommodative intraocular lens system as defined in claim 10 wherein:

said deformable connector comprises a first circular band and a second circular band and a central bridge extending between a peripheral portion of said first and second circular bands and a first outer bridge member extending between a perimeter of said first circular band and the perimeter of said first transparent structure and a second outer bridge member extending between a perimeter of said second circular band and the perimeter of said second transparent structure.

* * * * *